United States Patent [19]
Thim et al.

[11] Patent Number: 5,912,229
[45] Date of Patent: Jun. 15, 1999

[54] USE OF A PHARMACEUTICAL COMPOSITION COMPRISING AN APPETITE-SUPPRESSING PEPTIDE

[75] Inventors: Lars Thim, Gentofte; Birgitte Schjellerup Wulff, Virum; Martin Edward Judge, Copehagen; Ole Dragsbaek Madsen, Soborg; Jens Juul Holst, Hellerup, all of Denmark

[73] Assignee: Novo Nordisk Als, Bagsværd, Denmark

[21] Appl. No.: 08/808,825

[22] Filed: Feb. 28, 1997

Related U.S. Application Data

[60] Provisional application No. 60/015,403, Mar. 15, 1996, and provisional application No. 60/018,865, Mar. 15, 1996.

[30] Foreign Application Priority Data

Mar. 1, 1996 [DK] Denmark .................................. 0230/96
Mar. 1, 1996 [DK] Denmark .................................. 0231/96

[51] Int. Cl.⁶ ........................ A61K 38/26; C07K 14/605
[52] U.S. Cl. ............................ 514/12; 530/308; 530/324
[58] Field of Search ..................... 514/2, 12; 530/308, 530/324

[56] References Cited

U.S. PATENT DOCUMENTS 5,545,618  8/1996  Buckley et al. ........................ 514/12
5,635,564  6/1997  Wieditz et al. ........................ 525/194

FOREIGN PATENT DOCUMENTS

WO 93/18786  9/1993  WIPO .
WO 96/32414  10/1996  WIPO .

OTHER PUBLICATIONS

M.D. Turton et al., Nature vol. 379, pp. 69–72, (Jan. 1996).
J. Rachman et al., Diabetic Medicine, vol. 12, pp. 467–478 (1995).
Drucker et al., Proc. Natl. Acad. Sci. USA, vol. 93, pp. 7911–7916 (Jul. 1996).
Buhl et al., 'Natrually Occurring Products of Proglucagon 111–160 in Porcine and Human Small Intestine', The Journal of Biological Chemistry, vol. 263, No. 18, pp. 8621–8624, 1988.
Schmidt et al. 'Glucagon–Like Peptide–1 but not Glucagon––Like Peptide–2 Simulates Insulin Release from Isolated Rat Pancreatic Islets', Diabetolgia, vol. 28, No. 9, (abstract only), 1985.
Komatsu et al., 'Effect of Glucagon–Related Peptides on Rat Endocrine Pancreas', vol. 9, Suppl. 3, pp. 201–206 (abstract), 1988.
Mommsen et al. 'Glucagon–Like Peptides Activate Hepatic Gluconeogenesis', vol. 219, No. 1, pp. 227–232, 1987.
The Merck Manual, Sixth Edition, published 1992 by Merck Research Labratories, pp. 1108–1109, 1992.

*Primary Examiner*—Cecilia J. Tsang
*Assistant Examiner*—Anish Gupta
*Attorney, Agent, or Firm*—Steve T. Zelson, Esq.; Elias J. Lambiris, Esq.

[57] ABSTRACT

The present invention relates to appetite-suppressing peptides or an appetite-suppressing peptide-containing fraction for the treatment of obesity or type II diabetes.

17 Claims, 2 Drawing Sheets

Fig. 2

USE OF A PHARMACEUTICAL COMPOSITION COMPRISING AN APPETITE-SUPPRESSING PEPTIDE

CROSS-REFERENCE TO RELATED APPLICATIONS

This application claims priority of U.S. provisional applications 60/015,403 and 60/018,865 both filed Mar. 15, 1996 and of Danish applications 0230/96 filed Mar. 1, 1996 and 0231/96 filed Mar. 1, 1996, the contents of which applications are fully incorporated herein by reference.

FIELD OF INVENTION

The present invention relates to use of a pharmaceutical composition comprising an appetite-suppressing peptide or an appetite-suppressing peptide-containing fraction, as well as a method of obtaining appetite regulation by means of said peptide.

BACKGROUND OF THE INVENTION

Glucagon is produced by the pancreatic A-cell and released in response to low blood glucose levels. Its major site of action is the liver where it stimulates glucose production. It is thus the major hormone counteracting insulin in blood glucose homeostasis (Unger, R. H. and L. Orci (1990). Glucagon, in: *Diabetes Mellitus*, 4th ed. New York, Elsevier. pp 104–120).

Glucagon is processed from a larger precursor by limited proteolysis. Molecular cloning of the glucagon gene revealed that the proglucagon precursor contained not only glucagon but also two additional glucagon-like peptides named GLP-1 and GLP-2. GLP-1 and GLP-2 are encoded by separate exons suggesting distinct biological activities. It was later demonstrated that the proglucagon precursor was subjected to differential processing in the three different tissues known to produce proglucagon: the pancreatic A-cell, the intestinal L-cell, and in the central nervous system (CNS). Glucagon is thus selectively excised from the precursor in the islet A-cell, while GLP-1 and GLP-2 are selectively liberated from the intestinal L-cell and the CNS [reviewed in (Unger, R. H. and L. Orci (1990). Glucagon. in: *Diabetes Mellitus*, 4th ed. New York, Elsevier. pp 104–120)].

Specific GLP-1 receptors have been identified (Thorens, B. (1992) Proc. Natl. Acad. Sci. USA 89: 8641–8645) which are clearly distinct from the glucagon receptor (L. J Jelinek, et al. (1993) Science 259: 1614–1616) and they have different tissue distributions (R. V Campos, et al. (1994) Endocrinology 134: 2156–2164). GLP-1 is released from the L-cell after a meal and functions as an incretin hormone (i.e. it potentiates glucose induced insulin release from the pancreatic B-cell). The GLP-1 receptor is thus expressed at high levels on the surface of islet B-cells (K. Moens, et al. (1996) Diabetes 45: 257–261).

Induction of intestinal epithelial proliferation by GLP-2 was demonstrated (Drucker, D. J. et al (1996) Proc. Natl. Acad. Sci. USA 93: 7911–7916) and treatment of gastrointestinal deseases by cells grown in GLP-2 medium was disclosed (Drucker, D. J and Keneford, J. R., WO 96/32414).

No GLP-2 receptor has so far been reported.

Proglucagon derived peptides and feeding behaviour

We have previously reported the derivation and establishment of transplantable anorectic glucagonomas (O. D. Madsen et al. (1993) Endocrinology 133: 2022–2030) as well as of hypoglycemic insulinomas in the rat (O. D Madsen, et al. (1988) Proc. Natl. Acad. Sci. USA 85: 6652–6656). Such tumors can be derived from common clonal origin of pluripotent MSL-cells (O. D. Madsen, et al. (1986) J. Cell Biol. 103: 2025–2034) and reflects a maturation process towards islet A-cell and B-cells, respectively (O. D. Madsen, et al. (1993) Endocrinology 133: 2022–2030).

The glucagonoma associated anorexia is very severe: it has an acute onset and leads after few days to a complete stop in food intake. This severity of anorexia is hardly matched by other experimental tumors in rodents and suggests the production by the glucagonoma of a very powerful satiety factor which acts by a peripheral route of administration. It has previously been demonstrated that the anorectic glucagonomas displayed an unphysiological processing resulting in the formation of both glucagon and GLP-1 (O. D. Madsen, et al. (1993) Endocrinology 133: 2022–2030). Moreover, a non-anorectic glucagonoma variant was unable to process the precursor (O. D. Madsen, et al. (1995) Scand. J. Clin. Lab. Invest. 55, suppl 220: 27–36. Weight loss is mentioned as a component also of the glucagonoma syndrome in man (J. J. Holst (1985) Glucagon-producing tumors, in: *Hormone-producing tumors of the gastrointestinal tract*. New York, Churchill Livingstone. pp 57–84) although with a high degree of variability among different patients (S. J. Bhathena, et al. (1981). Glucagonoma and glucagonoma syndrome, in: *Glucagon. Physiology, pathophysiology and morphology of the pancreatic A-cells*. New York, Elsevier. 413–438).

Glucagon

Glucagon has been shown to be involved in the regulation of spontaneous meal size in rats but the overall effect is minimal and is exerted via the vagal connections to the liver (N. Geary, et al. (1993) Am. J. Physiol. 264: R116–R122). This effect is observed only by hepatic portal infusion of glucagon while intraperitoneal administration of pharmacological doses show no effect on food intake in fasted rats (O. D. Madsen, et al. (1993) Endocrinology 133: 2022–2030).

GLP-1

A central role for GLP-1 in the regulation of feeding was recently reported (M. D. Turton, et al. (1996) Nature 379: 69–72). Intracerebroventricular (ICV) administration of GLP-1 inhibited feeding in fasted rats. Again peripheral administration of GLP-1 had no effect on feeding behaviour (M. D. Turton, et al. (1996) Nature 379: 69–72; O. D. Madsen, et al. (1993) Endocrinology 133: 2022–2030) suggesting that tumor produced GLP-1 may not contribute significantly to the observed anorexia.

SUMMARY OF THE INVENTION

It has been found that GLP-2 has a powerful effect on inhibiting food intake when administered peripherally.

It is proposed that GLP-2 normally released together with GLP-1 from the intestinal L-cell serves its own distinct role as a peripheral satiety factor.

Figure 2:
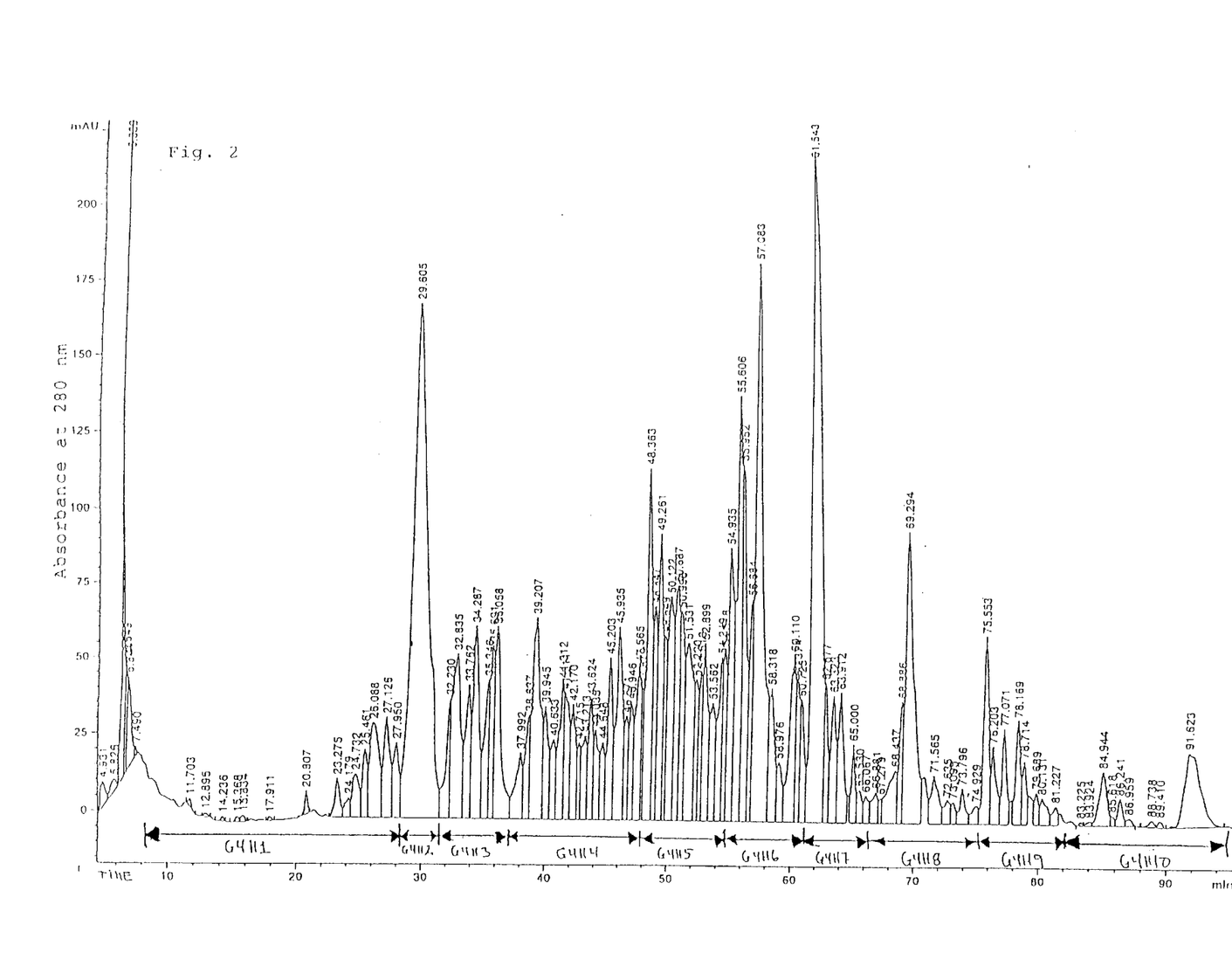
FIG. 2 A HPLC chromatogram of G4 material.

Accordingly, the present invention relates to use of a pharmaceutical composition comprising, together with a pharmaceutically acceptable excipient or vehicle, an HPLC fraction of a glucagonoma tumour extract prepared by acid ethanol extraction, gel filtration and preparative HPLC, said fraction being shown as fraction G4H9 in FIG. 2 and containing glucagon-like peptide 2 (GLP-2) as a major component (i.e. more than 40%) or comprising any single component of said fraction or a combination of two or more of the components of said fraction.

In another aspect, the invention relates to use of a pharmaceutical composition comprising glucagon-like peptide-2

(GLP-2) or a variant or homologue thereof for the prohylaxis or treatment of diseases or disorders associated with impaired appetite regulation.

In a further aspect, the invention relates to use of a pharmaceutical composition comprising a peptide with the following amino acid sequence wherein $X^1$ is $NH_2$, DFPEEVAIVEELGRR (SEQ ID NO:2), DFPEEVTIVEELGRR (SEQ ID NO:3), DFPEEVNIVEELRRR (SEQ ID NO:4), or a fragment thereof, $X^2$ is Ala or Gly, $X^3$ is Ile or Val, $X^4$ is Asn, Ser or His, $X^5$ is Ala or Thr, $X^6$ is Arg or Lys, $X^7$ is Ile or Leu, $X^8$ is Gln or His, or $X^9$ is OH, Lys, Arg, Arg-Lys, Lys-Arg, Arg-Arg or Lys-Lys for the prophylaxis or treatment of diseases or disorders associated with impaired appetite regulation.

In a still further aspect, the invention relates to method of treating diseases or disorders associated with impaired appetite regulation, the method comprising administering to an individual in need of such treatment an amount of a peptide as specified herein sufficient to suppress appetite or induce satiety in said individual.

In a still further aspect, the invention relates to the use of a peptide as specified herein for the manufacture of a medicament for the prophylaxis or treatment of diseases or disorders associated with impaired appetite regulation.

DETAILED DESCRIPTION OF THE INVENTION

In the present description, the term "peptide" is understood to include the mature GLP-2 peptide or a precursor form thereof as well a functional fragment thereof which essentially has the activity of the full-length peptide. Furthermore, the term "peptide" is intended to include homologues of said peptide. Such homologues comprise an amino acid sequence exhibiting a degree of identity of at least 50%, such as at least 75%, and more particularly at least 90% identity with the amino acid sequence of human GLP-2. The degree of identity may be determined by conventional methods, see for instance, Altshul et al., i Bull. Math. Bio. 48: 603–616, 1986, and Henikoff and Henikoff, Proc. Natl. Acad. Sci. USA 89: 10915–10919, 1992.

Homologues of the present peptide may have one or more amino acid substitutions, deletions or additions. These changes may be of a minor nature, that is conservative amino acid substitutions that do not significantly affect the folding or activity of the peptide, small deletions, typically of one to about five amino acids, small amino- or carboyxyl-terminal extensions, such as an amino-terminal methionine residue, a small linker peptide of up to about 15 residues, or a small extension that facilitates purification, such as a poly-histidine tract, an antigenic epitope or a binding domain. See in general Ford et al., *Protein Expression and Purification* 2: 95–107, 1991. Examples of conservative substitutions are within the group of basic amino acids (such as arginine, lysine, histidine), acidic amino acids (such as glutamic acid and aspartic acid), polar amino acids (such as glutamine and asparagine), hydrophobic amino acids (such as leucine, isoleucine, valine), aromatic amino acids (such as phenylalanine, tryptophan, tyrosine) and small amino acids (such as glycine, alanine, serine, threonine, methionine).

The homologue may be an allelic variant, i.e. an alternative form of a gene that arises through mutation, or an altered peptide encoded by the mutated gene, but having substantially the same activity as the native GLP-2 peptide. Hence mutations can be silent (no change in the encoded peptide) or may encode peptides having altered amino acid sequence.

The homologue of the present peptide may also be a species homologue, i.e. a peptide with a similar activity derived from another species. Examples of species homologues of the GLP-2 peptide are human, bovine, rat, hamster, guinea pig and porcine GLP-2.

In a preferred embodiment of the present invention, the GLP-2 peptide is one in which $X^1$ is $NH_2$, $X^2$ is Ala, $X^3$ is Ile, $X^4$ is Asn, $X^5$ is Ala, $X^6$ is Arg, $X^7$ is Ile, $X^8$ is Gln, or $X^9$ is OH. In particular, the peptide has the following amino acid sequence A homologue of the peptide may be isolated by preparing a genomic or cDNA library of a cell of the species in question, and screening for DNA sequences coding for all or part of the homologue by using synthetic oligonucleotide probes in accordance with standard techniques, e.g. as described by Sambrook et al., *Molecular Cloning:A Laboratory Manual*, 2nd. Ed. Cold Spring Harbor Laboratory, Cold Spring Harbor, N.Y., 1989, or by means of polymerase chain reaction (PCR) using specific primers as described by Sambrook et al., supra.

The present invention also relates to a composition comprising a variant of the GLP-2 peptide. The variant is one in which one or more amino acid residues have been substituted by other amino acid residues. In a particularly preferred embodiment Ala has been substituted by Gly in position 2 of the mature peptide. It is expected that this variant will exhibit a longer plasma half-life than the native peptide, which is an advantage because the dosage required to obtain an adequate appetite-suppressing or satiety-inducing effect will generally be smaller.

The GLP-2 peptide or homologue or variant thereof as specified above may be made by recombinant DNA techniques in accordance with procedures well established in the art.

More specifically, a DNA sequence encoding the GLP-2 peptide may be isolated or synthesized on the basis of the published human preproglucagon DNA sequence (cf. J. W. White et al., *Nucleic Acids Res.* 14, 1986, pp. 4719–4730; G. I. Bell et al., *Nature* 304, 1983, pp. 368–371), for instance obtained by preparing a genomic or cDNA library from an appropriate tissue and screening for DNA sequences coding for all or part of the GLP-2 peptide by hybridization using synthetic oligonucleotide probes in accordance with standard techniques (cf. Sambrook et al., supra). For the present purpose, the DNA sequence encoding the GLP-2 peptide is preferably of human origin.

The DNA construct encoding the GLP-2 peptide may also be prepared synthetically by established standard methods, e.g. the phosphoamidite method described by Beaucage and Caruthers, *Tetrahedron Letters* 22 (1981), 1859–1869, or the method described by Matthes et al., *EMBO Journal* 3 (1984), 801–805. According to the phosphoamidite method, oligonucleotides are synthesized, e.g. in an automatic DNA synthesizer, purified, annealed, ligated and cloned in suitable vectors.

Furthermore, the DNA construct may be of mixed synthetic and genomic, mixed synthetic and cDNA or mixed genomic and cDNA origin prepared by ligating fragments of synthetic, genomic or cDNA origin (as appropriate), the fragments corresponding to various parts of the entire DNA construct, in accordance with standard techniques.

The DNA construct may also be prepared by polymerase chain reaction using specific primers, for instance as described in U.S. Pat. No. 4,683,202 or Saiki et al., *Science* 239 (1988), 487–491, or Sambrook et al., supra.

In a currently preferred embodiment, the DNA construct comprises the DNA sequence shown in FIG. 3 of G. I. Bell et al., *Nature* 304, 1983, pp. 368–371, as well as nucleic acid sequences encoding human GLP-2, but which differ from the DNA sequence shown in FIG. 3 of Bell et al., supra, by virtue of the degeneracy of the genetic code. The DNA construct further includes nucleic acid sequences which hybridize to a nucleic acid molecule (either genomic, synthetic or cDNA or RNA) encoding human GLP-2 under the conditions of high stringency (i.e. presoaking in 5X SSC and prehybridizing for 1 hr at about 40° C. in a solution of 20% formamide, 5X Denhardt's solution, 50 mM sodium phosphate, pH 6.8, and 50 $\mu$g denatured sonicated calf thymus DNA, followed by hybridization in the same solution supplemented with 100 $\mu$M ATP for 18 hrs. at about 40° C., followed by a wash in 0.4X SSC at a temperature of about 45° C.). This could, for instance, be DNA sequences encoding GLP-2 from other species, e.g. rat, bovine, hamster, guinea pig or porcine GLP-2.

To express GLP-2, the DNA construct encoding the GLP-2 peptide is inserted into an appropriate recombinant vector. This may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the GLP-2 peptide is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the peptide.

The promoter may be any DNA sequence which shows transcriptional activity in the host cell of choice and may be derived from genes encoding proteins either homologous or heterologous to the host cell.

Examples of suitable promoters for directing the transcription of the DNA encoding the GLP-2 peptide in mammalian cells are the SV40 promoter (Subramani et al., *Mol. Cell Biol.* 1 (1981), 854–864), the MT-1 (metallothionein gene) promoter (Palmiter et al., *Science* 222 (1983), 809–814) or the adenovirus 2 major late promoter.

An example of a suitable promoter for use in insect cells is the polyhedrin promoter (U.S. Pat. No. 4,745,051; Vasuvedan et al., *FEBS Lett.* 311, (1992) 7–11), the P10 promoter (J. M. Vlak et al., *J. Gen. Virology* 69, 1988, pp. 765–776), the *Autographa californica* polyhedrosis virus basic protein promoter (EP 397 485), the baculovirus immediate early gene 1 promoter (U.S. Pat. No. 5,155,037; U.S. Pat. No. 5,162,222), or the baculovirus 39K delayed-early gene promoter (U.S. Pat. No. 5,155,037; U.S. Pat. No. 5,162,222).

Examples of suitable promoters for use in yeast host cells include promoters from yeast glycolytic genes (Hitzeman et al., *J. Biol. Chem.* 255 (1980), 12073–12080; Alber and Kawasaki, *J. Mol. Appl. Gen.* 1 (1982), 419–434) or alcohol dehydrogenase genes (Young et al., in *Genetic Engineering of Microorganisms for Chemicals* (Hollaender et al, eds.), Plenum Press, New York, 1982), or the TPI1 (U.S. Pat. No. 4,599,311) or ADH2-4c (Russell et al., *Nature* 304 (1983), 652–654) promoters.

Examples of suitable promoters for use in filamentous fungus host cells are, for instance, the ADH3 promoter (McKnight et al., *The EMBO J.* 4 (1985), 2093–2099) or the tpiA promoter. Examples of other useful promoters are those derived from the gene encoding *A. oryzae* TAKA amylase, *Rhizomucor miehei* aspartic proteinase, *A. niger* neutral α-amylase, *A. niger* acid stable α-amylase, *A. niger* or *A. awamori* glucoamylase (gluA), *Rhizomucor miehei* lipase, *A. oryzae* alkaline protease, *A. oryzae* triose phosphate isomerase or *A. nidulans* acetamidase. Preferred are the TAKA-amylase and gluA promoters.

Examples of suitable promoters for use in bacterial host cells include the promoter of the *Bacillus stearothermophilus* maltogenic amylase gene, the *Bacillus licheniformis* alpha-amylase gene, the *Bacillus amyloliquefaciens* BAN amylase gene, the *Bacillus subtilis* alkaline protease gen, or the *Bacillus pumilus* xylosidase gene, or by the phage Lambda $P_R$ or $P_L$ promoters or the *E. coli* lac, trp or tac promoters.

The DNA sequence encoding the GLP-2 peptide may also, if necessary, be operably connected to a suitable terminator, such as the human growth hormone terminator (Palmiter et al., op. cit.) or (for fungal hosts) the TPI1 (Alber and Kawasaki, op. cit.) or ADH3 (McKnight et al., op. cit.) terminators. The vector may further comprise elements such as polyadenylation signals (e.g. from SV40 or the adenovirus 5 Elb region), transcriptional enhancer sequences (e.g. the SV40 enhancer) and translational enhancer sequences (e.g. the ones encoding adenovirus VA RNAs).

The recombinant vector may further comprise a DNA sequence enabling the vector to replicate in the host cell in question. An example of such a sequence (when the host cell is a mammalian cell) is the SV40 origin of replication.

When the host cell is a yeast cell, suitable sequences enabling the vector to replicate are the yeast plasmid 2$\mu$ replication genes REP 1–3 and origin of replication.

The vector may also comprise a selectable marker, e.g. a gene the product of which complements a defect in the host cell, such as the gene coding for dihydrofolate reductase (DHFR) or the *Schizosaccharomyces pombe* TPI gene (described by P. R. Russell, Gene 40, 1985, pp. 125–130), or one which confers resistance to a drug, e.g. ampicillin, kanamycin, tetracyclin, chloramphenicol, neomycin, hygromycin or methotrexate. For filamentous fungi, selectable markers include amdS, pyrG, argB, niaD, sC.

To direct the GLP-2 peptide into the secretory pathway of the host cells, a secretory signal sequence (also known as a leader sequence, preprosequence or presequence) may be provided in the recombinant vector. The secretory signal sequence is joined to the DNA sequence encoding the peptide in the correct reading frame. Secretory signal sequences are commonly positioned 5' to the DNA sequence encoding the peptide. The secretory signal sequence may be that normally associated with the peptide or may be from a gene encoding another secreted protein.

For secretion from yeast cells, the secretory signal sequence may encode any signal peptide which ensures efficient direction of the expressed peptide into the secretory pathway of the cell. The signal peptide may be naturally occurring signal peptide, or a functional part thereof, or it may be a synthetic peptide. Suitable signal peptides have been found to be the α-factor signal peptide (cf. U.S. Pat. No. 4,870,008), the signal peptide of mouse salivary amylase (cf. O. Hagenbuchle et al., *Nature* 289, 1981, pp. 643–646), a modified carboxypeptidase signal peptide (cf. L. A. Valls et al., *Cell* 48, 1987, pp. 887–897), the yeast BAR1 signal peptide (cf. WO 87/02670), or the yeast aspartic protease 3 (YAP3) signal peptide (cf. M. Egel-Mitani et al., *Yeast* 6, 1990, pp. 127–137).

For efficient secretion in yeast, a sequence encoding a leader peptide may also be inserted downstream of the signal sequence and upstream of the DNA sequence encoding the GLP-2 peptide. The function of the leader peptide is to allow the expressed peptide to be directed from the endoplasmic reticulum to the Golgi apparatus and further to a secretory vesicle for secretion into the culture medium (i.e. export of the peptide across the cell wall or at least through the cellular membrane into the periplasmic space of the yeast cell). The leader peptide may be the yeast α-factor leader (the use of which is described in e.g. U.S. Pat. No. 4,546,082, EP 16 201, EP 123 294, EP 123 544 and EP 163 529). Alternatively, the leader peptide may be a synthetic leader peptide, which is to say a leader peptide not found in nature. Synthetic leader peptides may, for instance, be constructed as described in WO 89/02463 or WO 92/11378.

For use in filamentous fungi, the signal peptide may conveniently be derived from a gene encoding an Aspergillus sp. amylase or glucoamylase, a gene encoding a *Rhizomucor miehei* lipase or protease, a *Humicola lanuginosa* lipase. The signal peptide is preferably derived from a gene encoding *A. oryzae* TAKA amylase, *A. niger* neutral α-amylase, *A. niger* acid-stable amylase, or *A. niger* glucoamylase.

For use in insect cells, the signal peptide may conveniently be derived from an insect gene (cf. WO 90/05783), such as the lepidopteran *Manduca sexta* adipokinetic hormone precursor signal peptide (cf. U.S. Pat. No. 5,023,328).

The procedures used to ligate the DNA sequences coding for the GLP-2 peptide, the promoter and optionally the terminator and/or secretory signal sequence, respectively, and to insert them into suitable vectors containing the information necessary for replication, are well known to persons skilled in the art (cf., for instance, Sambrook et al., op.cit.).

The DNA sequence encoding the GLP-2 peptide introduced into the host cell may be either homologous or heterologous to the host in question. If homologous to the host cell, i.e. produced by the host cell in nature, it will typically be operably connected to another promoter sequence or, if applicable, another secretory signal sequence and/or terminator sequence than in its natural environment. The term "homologous" is intended to include a cDNA sequence encoding a polypeptide native to the host organism in question. The term "heterologous" is intended to include a DNA sequence not expressed by the host cell in nature. Thus, the DNA sequence may be from another organism, or it may be a synthetic sequence.

The host cell into which the DNA construct or the recombinant vector of the invention is introduced may be any cell which is capable of producing the present peptide and includes bacteria, yeast, fungi and higher eukaryotic cells.

Examples of bacterial host cells which, on cultivation, are capable of producing the GLP-2 peptide are grampositive bacteria such as strains of Bacillus, such as strains of *B. subtilis, B. licheniformis, B. lentus, B. brevis, B. stearothemophilus, B. alkalophilus, B. amyloliquefaciens, B. coagulans, B. circulans, B. lautus, B. megatherium* or *B. thuringiensis,* or strains of Streptomyces, such as *S. lividans* or *S. murinus,* or gramnegative bacteria such as *Echerichia coli.* The transformation of the bacteria may be effected by protoplast transformation or by using competent cells in a manner known per se (cf. Sambrook et al., supra).

When expressing the peptide in bacteria such as *E. coli,* the peptide may be retained in the cytoplasm, typically as insoluble granules (known as inclusion bodies), or may be directed to the periplasmic space by a bacterial secretion sequence. In the former case, the cells are lysed and the granules are recovered and denatured after which the peptide is refolded by diluting the denaturing agent. In the latter case, the peptide may be recovered from the periplasmic space by disrupting the cells, e.g. by sonication or osmotic shock, to release the contents of the periplasmic space and recovering the peptide.

Examples of suitable mammalian cell lines are the COS (ATCC CRL 1650), BHK (ATCC CRL 1632, ATCC CCL 10), CHL (ATCC CCL39) or CHO (ATCC CCL 61) cell lines. Methods of transfecting mammalian cells and expressing DNA sequences introduced in the cells are described in e.g. Kaufman and Sharp, *J. Mol. Biol.* 159 (1982), 601–621; Southern and Berg, *J. Mol. Appi. Genet.* 1 (1982), 327–341; Loyter et al., *Proc. Natl. Acad. Sci. USA* 79 (1982), 422–426; Wigler et al., *Cell* 14 (1978), 725; Corsaro and Pearson, *Somatic Cell Genetics* 7 (1981), 603, Graham and van der Eb, *Virology* 52 (1973), 456; and Neumann et al., *EMBO J.* 1 (1982), 841–845.

Examples of suitable yeasts cells include cells of Saccharomyces spp. or Schizosaccharomyces spp., in particular strains of *Saccharomyces cerevisiae* or *Saccharomyces kluyveri*. Methods for transforming yeast cells with heterologous DNA and producing heterologous polypeptides therefrom are described, e.g. in U.S. Pat. Nos. 4,599,311, 4,931,373, 4,870,008, 5,037,743, and U.S. Pat. No. 4,845, 075, all of which are hereby incorporated by reference. Transformed cells are selected by a phenotype determined by a selectable marker, commonly drug resistance or the ability to grow in the absence of a particular nutrient, e.g. leucine. A preferred vector for use in yeast is the POT1 vector disclosed in U.S. Pat. No. 4,931,373. The DNA sequence encoding the GLP-2 peptide may be preceded by a signal sequence and optionally a leader sequence, e.g. as described above. Further examples of suitable yeast cells are strains of Kluyveromyces, such as *K. lactis,* Hansenula, e.g. *H. polymorpha,* or Pichia, e.g. *P. pastoris* (cf. Gleeson et al., *J. Gen. Microbiol.* 132, 1986, pp. 3459–3465; U.S. Pat. No. 4,882,279).

Examples of other fungal cells are cells of filamentous fungi, e.g. Aspergillus spp., Neurospora spp., Fusarium spp. or Trichoderma spp., in particular strains of *A. oryzae, A. nidulans* or *A. niger*. The use of Aspergillus spp. for the expression of proteins is described in, e.g., EP 272 277 and EP 230 023. The transformation of *F. oxysporum* may, for instance, be carried out as described by Malardier et al., 1989, Gene 78: 147–156.

When a filamentous fungus is used as the host cell, it may be transformed with the DNA construct encoding the GLP-2 peptide, conveniently by integrating the DNA construct in the host chromosome to obtain a recombinant host cell. This integration is generally considered to be an advantage as the DNA sequence is more likely to be stably maintained in the cell. Integration of the DNA constructs into the host chromosome may be performed according to conventional methods, e.g. by homologous or heterologous recombination.

Transformation of insect cells and production of heterologous polypeptides therein may be performed as described in U.S. Pat. Nos. 4,745,051; 4,879,236; 5,155,037; 5,162,222; EP 397,485) all of which are incorporated herein by reference. The insect cell line used as the host may suitably be a Lepidoptera cell line, such as *Spodoptera frugiperda* cells or *Trichoplusia ni* cells (cf. U.S. Pat. No. 5,077,214). Culture conditions may suitably be as described in, for instance, WO 89/01029 or WO 89/01028, or any of the aforementioned references.

The transformed or transfected host cell described above is then cultured in a suitable nutrient medium under conditions permitting the expression of the GLP-2 peptide, after which the resulting GLP-2 peptide is recovered from the culture.

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The GLP-2 peptide produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e. g. ion exchange chromatography, gelfiltration chromatography, affinity chromatography, or the like.

In the pharmaceutical composition of the invention, the GLP-2 peptide may be formulated by any of the established methods of formulating pharmaceutical compositions, e.g. as described in *Remington's Pharmaceutical Sciences*, 1985. The composition may be in a form suited for systemic injection or infusion and may, as such, be formulated with a suitable liquid vehicle such as sterile water or an isotonic saline or glucose solution. The compositions may be sterilized by conventional sterilization techniques which are well known in the art. The resulting aqueous solutions may be packaged for use or filtered under aseptic conditions and lyophilized, the lyophilized preparation being combined with the sterile aqueous solution prior to administration. The composition may contain pharmaceutically acceptable auxiliary substances as required to approximate physiological conditions, such as buffering agents, tonicity adjusting agents and the like, for instance sodium acetate, sodium lactate, sodium chloride, potassium chloride, calcium chloride, etc.

The pharmaceutical composition of the present invention may also be adapted for nasal, transdermal, pulmonal or rectal administration. The pharmaceutically acceptable carrier or diluent employed in the composition may be any conventional solid carrier. Examples of solid carriers are lactose, terra alba, sucrose, talc, gelatin, agar, pectin, acacia, magnesium stearate and stearic acid. Similarly, the carrier or diluent may include any sustained release material known in the art, such as glyceryl monostearate or glyceryl distearate, alone or mixed with a wax.

It may be of particular advantage to provide the composition of the invention in the form of a sustained release formulation. As such, the composition may be formulated as microcapsules or microparticles containing the GLP-2 peptide encapsulated by or dispersed in a suitable pharmaceutically acceptable biodegradable polymer such as polylactic acid, polyglycolic acid or a lactic acid/glycolic acid copolymer.

For nasal administration, the preparation may contain GLP-2 peptide dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

Generally, the compounds of the present invention are dispensed in unit dosage form comprising 0.5–500 mg of the peptide together with a pharmaceutically acceptable carrier per unit dosage.

The GLP-2 peptide is contemplated to be advantageous to use in appetite suppression or satiety induction, such as for the prophylaxis or treatment of diseases or disorders associated with impaired appetite regulation. Examples of such diseases or disorders are obesity and type II diabetes. The dosage of the GLP-2 peptide administered to a patient will vary with the type and severity of the condition to be treated, but is generally in the range of from about 10 $\mu$g/kg to about 5 mg/kg body weight.

In the pharmaceutical composition of the invention, the GLP-2 peptide may be combined with another appetite-suppressing or satiety-inducing agent. An example of such an agent is GLP-1 which has been shown to have some effect on appetite suppression (cf. M. D. Turton et al., *Nature* 379, Jan. 4, 1996, pp. 69–72).

It is further contemplated that the GLP-2 peptide in suitably labelled form, e.g. radiolabelled GLP-2, may be used to identify a receptor for GLP-2 in binding studies using tissue(s) expected to express the GLP-2 receptor, e.g. hypothalamus tissue. Once localized by GLP-2 binding, the receptor may be cloned by expression cloning, i.e. by preparing a cDNA library of the tissue in question, cloning the cDNA into suitable vectors and introducing the vectors into an appropriate cell to effect expression of the cDNA, after which a clone expressing the receptor is identified by binding to GLP-2. A cell line stably expressing the receptor may then be used in a screening assay for GLP-2 agonists (i.e. compounds acting on the receptor to induce satiety or suppress appetite) or GLP-2 antagonists (i.e. compounds which antagonize the action of GLP-2 on the receptor, e.g. for use in the treatment of cancer anorexia or anorexia nervosa).

The invention is further illustrated in the following examples which are not in any way intended to limit the scope of the invention as claimed.

EXAMPLE 1

Acid Ethanol Extraction Of Tumor Tissue

Anorectic tumors were produced in rats as previously described (Madsen, O.D. et al. (1993) Endocrinology 133, 2022–2030). Fifty anorectic 12C3AN (MSL-G-AN) tumours (at −80° C.) corresponding to 50.07 g of wet tissue were homogenised at 4° C. with 700 ml of acid ethanol (96% ethanol/0.7M HCl, 3/1, vol/vol). The homogenisation was carried out for 5 min in a precooled (4° C.) 2 liter Waring Commercial Blender at maximum speed. After homogenisation the mixture was stirred at 4° C. for 16 hours. The mixture was centrifuged at 9000 RPM at 4° C. for 1 hour. The volume of the supernatant was reduced to 20% by vacuum rotation. During this process, in which the main part of the ethanol is removed, some precipitate is formed. This precipitate was removed by centrifugation at 4° C. for one hour at 20.000 RPM. The supernatant, which still contained some lipid-like material, was filtered and applied to a LiChroprep RP-18 (Merck) column (2.5×10 cm) equilibrated with 0.1% TFA at a flow rate of 2 ml/min. The column was washed with 100 ml of 0.1% of TFA at a flow rate of 4 ml/min. Bound material was eluted with 400 ml of 0.1% TFA containing 70% (vol/vol) of acetonitrile. The acetonitrile was removed by vacuum rotation and the resulting mixture was lyophilised. After lyophilization the material was dissolved in 50 ml of water and the pH was adjusted to 5.3 with 425 μl of 1N NaOH. Further titration of the mixture to pH 6.0 resulted in the formation of a precipitate. Upon back titration to pH 5.3 this precipitate was dissolved again. Therefore the pH was left at 5.3 and the mixture was lyophilised. The total yield of lyophilised material from 50 tumours was 359 mg of dry powder.

EXAMPLE 2

First Purification Step: Gel Filtration On Sephadex G-75

Figure 1:
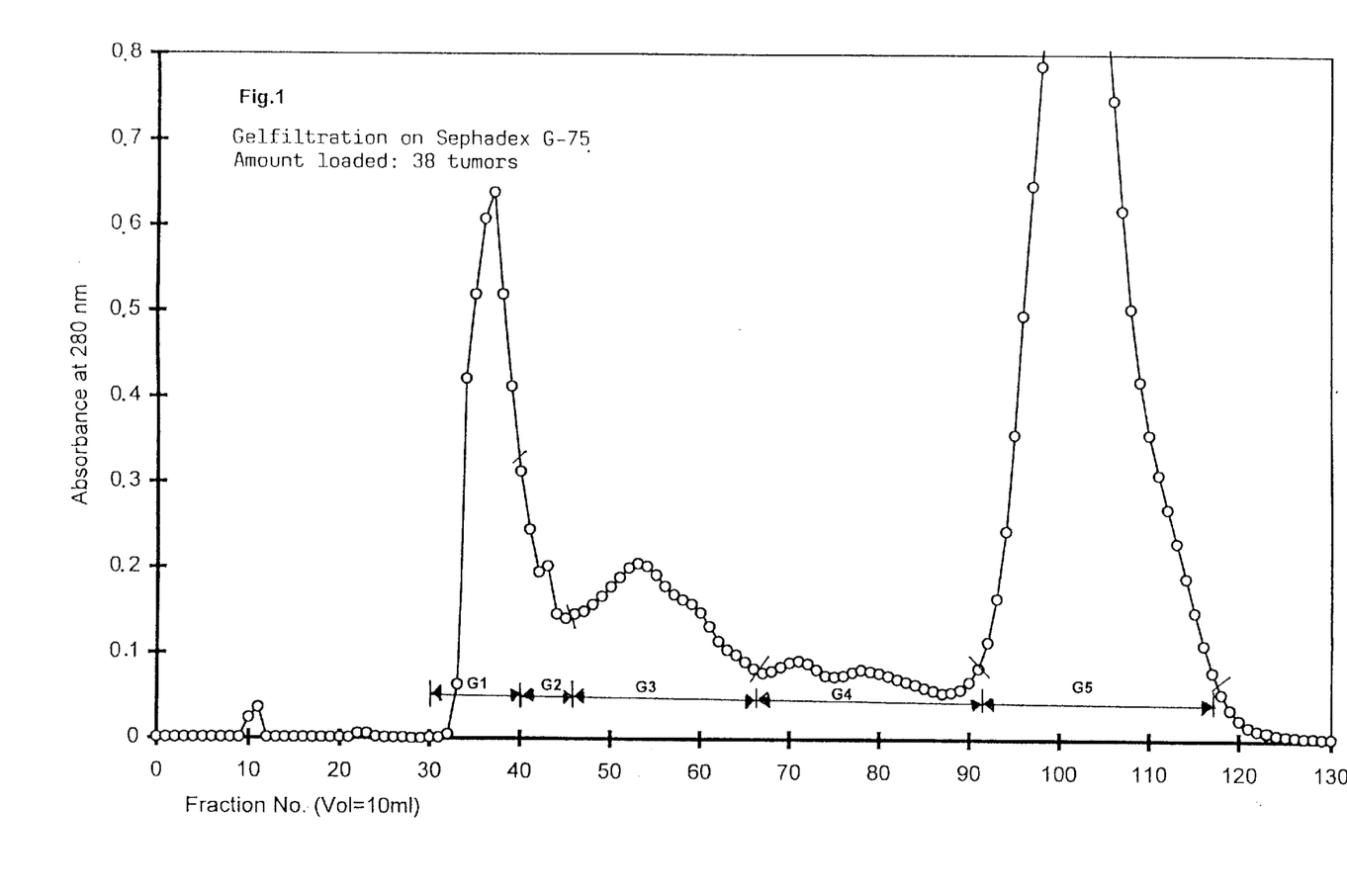
FIG. 1 A gel filtration chromatogram of fractions G1, G2, G3, G4, and G5.

Lyophilized material (278 mg) from the acid ethanol extract corresponding to 38 individual tumors was redissolved in 20 ml of 1 M HAc and applied to Sephadex G75 column (5×50 cm). The column was equilibrated and eluted with 1 M HAc at a flow rate of 55 ml/h, and fractions corresponding to 10 ml were collected. The absorption at 280 nm was recorded for each fraction. The gel filtration chromatogram is shown in FIG. 1. Individual fractions were pooled in the following 5 main fractions: G1 (Fr. 30–39), G2 (Fr. 40–45), G3 (Fr. 46–66), G4 (Fr. 67–91) and G5 (Fr. 92–118) and subjected to bioassay after lyophilization.

EXAMPLE 3

Second Purification Step: Preparative HPLC Of The G4 Pool

Some of the appetite suppression activity of gel filtration pools showed the activity to be present in the G4 pool, and this pool was further fractionated by preparative HPLC. Lyophilized G4 material (corresponding to 80 tumors) was redissolved in 15 ml 0.1% TFA and pumped onto a Vydac 214TP1022 C4 column (2.2×25 cm) equilibrated in 0.1% TFA. The column was washed with 20 ml of 0.1% TFA, followed by 100 ml of MeCN/$H_2O$/TFA (10.0:89.9:0.1, v/v/v). The material was eluted at 25° C. at a flow rate of 4 ml/min with a linear gradient formed from MeCN/$H_2O$/TFA (10:79.9:0.1, v/v/v) and MeCN/$H_2O$/TFA (65.0:34.9:0.1, v/v/v) over 110 min. UV absorption was monitored at 214 nm and 280 nm. The HPLC chromatogram (monitored at 280 nm) is shown in FIG. 2. Fractions corresponding to 10 main pools were generated as indicated in FIG. 2. The volume was reduced to approx. 25% by vacuum rotation and the fractions were lyophilized and tested in the bioassay.

The appetite suppression activity was found in fraction G4H9 (Example 6) and the peptides of this fraction were analysed by amino acid sequence analysis and mass spectrometry analysis (Example 4).

EXAMPLE 4

Chemical Characterisation Of The Peptides In Fraction G4H9

Amino acid sequence analysis was carried out by automated Edman degradation using an Applied Biosystems Model 477 gas-phase sequencer essentially as described by the manufacturer. Mass spectrometry analysis was performed using an API III LC/MS/MS system (Sciex, Thornhill, Ont., Canada). The triple quadrupole instrument has a mass-to-charge (m/z) range of 2400 and is fitted with a pneumatically assisted electrospray (also referred to as ion-spray) interface (Bruins, A. P., Covey, T. R., & Henion, J. D. (1987) *Anal. Chem.* 59, 2642–2646 and Covey, T. R., Bonner, R. F., Shushan, B. I., & Henion, J. D. (1988) *Rapid Commun. Mass Spectrom.* 2, 249–256). Sample introduction was done by a syringe infusion pump (Sage Instruments, Cambridge, Mass.) through a fused capillary /75 mm i.d.) with a liquid flow rate set at 0.5–1 ml/min. The instrument m/z scale was calibrated with the singly-charged ammonium adduct ions of poly(propylene glycols) (PPGs) under unit resolution. The accuracy of mass measurements is generally better than 0.02%.

Fraction G4H9:

The dominating peptide in this fraction was found to have the following amino acid sequence:

H A D G S F S D E M N T I L D N L A T R D F I N W L I Q T K I T D (SEQ ID NO:6)

The molecular weight found by mass spectrometry was: 3796.

This peptide is identical to rat GLP-2 (1–33). Minor amounts of the following two peptides were also found:

D F P E E V A I A E E L G R R H A D G S F S D E M N T I L D N L A T R D F I N W L I Q T K I T D (SEQ ID NO:8) and H D E F E R H A E G T F T S D V S S Y L E G Q A A K E F I A W L V K G R (SEQ ID NO:9)

These peptides are identical to rat GLP-2 which is N-terminally extended with spacer peptide 2 and rat GLP-1 (1–36amide), respectively.

EXAMPLE 5

Test Method For Measuring Appetite Suppression In Mice

Mice were deprived of their normal feed for two days and given free access to a 20% sucrose solution on the first day of feed deprivation. After the 2-day feed deprivation period, mice were injected intraperitoneally with 0.5 ml of a solution containing the test substance. Thirty minutes after injection, individual mice were placed in one of eight 15 $cm^2$ test box with a stainless steel grid floor and a glass drinking tube which projected into the box. The drinking tube was connected to a reservoir containing a 20% sucrose solution, and the interior of the drinking tube contained an electrode enabling the detection of drinking contacts with the solution by measuring the flow of a weak (unnoticeable) electric current through mice by means of an electronic apparatus connected to the drinking tube electrode and the stainless steel grid floor. Consumption of the sucrose solution was measured over a 10 minute period by electronically recording the total amount of contact with the sucrose solution during the test session. The degree of appetite suppression produced by a given test substance was determined by statistical comparison of the duration of sucrose consumption by control (vehicle treated) mice with that of mice treated with a test substance. The degree of appetite suppression in a treated group of mice was expressed as percent of the control groups response.

EXAMPLE 6

Test For Appetite Suppression In Mice By Fractions Containing GLP-2.

Mice were tested for appetite suppression (see Example 5) after treatment with a test substance. The test substance consisted of extracts of the anorectic glucagonoma tumor prepared according to Example 3 (Gelfiltration fraction G4) or according to Example 4 (HPLC fraction G4H9) dissolved in phosphate buffered saline. The test solution containing lyophilized material from the Gelfiltration fraction G4 corresponding to 3.3 tumors suppressed sucrose consumption by 72%. Of the 10 HPLC sub-fractions of the G4 Gelfiltration fraction (see Example 4 and FIG. 2), only the GLP-2 containing fraction, G4H9, gave a statistically significant suppression of appetite, suppressing sucrose consumption by 49%, when lyophilized material corresponding to 5.3 tumors was given.

EXAMPLE 7

Test For Appetite Suppression In Mice By Synthetic GLP-2

Mice were tested for appetite suppression as described in Example 5 after treatment with a test substance consisting of synthetic porcine GLP-2 dissolved in phosphate buffered saline. Porcine GLP-2 has the following amino acid sequence:

H A D G S F S D E M N T V L D N L A T R D F I N W L L H T K I T D (SEQ ID NO:7).

An intraperitoneal injection of test solution containing 50 micrograms of synthetic porcine GLP-2 suppressed sucrose consumption by 38%.

EXAMPLE 8

Test Method For Measuring Appetite Suppression In Mice

The method is as in Example 5, but instead of 20% sucrose, a solution of infant formula milk (Complan®) is used. The test substance is dissolved in a vehicle consisting of phosphate buffered saline with 1% albumin. Test substances dissolved in vehicle are injected either intravenously (IV) in a volume of 100 microliters, or intracerebroventricularly (ICV) in a volume of 10 microliters.

EXAMPLE 9

Test For Appetite Suppression In Mice By Synthetic GLP-2

Mice were tested for appetite suppression as described in Example 8 after treatment with a test substance consisting of synthetic human GLP-2. Human GLP-2 has the following amino acid sequence:

H A D G S F S D E M N T I L D N L A A R D F I N W L I Q T K I T D (SEQ ID NO:5).

An IV injection of test solution containing 3 micrograms of synthetic human GLP-2 suppressed milk consumption by 24%, while ICV injections of 3 micrograms and 10 micrograms of synthetic human GLP-2 suppressed milk consumption by 32% and 35%, respectively.

We claim:

1. A method of treating diseases or disorders associated with impaired appetite regulation, comprising administering to an individual in need of such treatment a pharmaceutical composition comprising a pharmaceutically acceptable excipient or vehicle and an effective amount of a peptide having the following amino acid sequence (SEQ ID NO: 1)

$X^1$ H $X^2$ D G S F S D E M N T $X^3$ L D $X^4$ L A $X^5$ $X^6$ D F I N W L $X^7$ $X^8$ T K I T D $X^9$ wherein $X^1$ is $NH_2$, DFPEEVAIVEELGRR (SEQ ID NO:2), DFPEEVTIVEELGRR (SEQ ID NO:3), DFPEEVNIVEELRRR (SEQ ID NO:4), or a fragment thereof, $X^2$ is Ala or Gly, $X^3$ is Ile or Val, $X^4$ is Asn, Ser or His, $X^5$ is Ala or Thr, $X^6$ is Arg or Lys, $X^7$ is Ile or Leu, $X^8$ is Gln or His, and $X^9$ is OH, Lys, Arg, Arg-Lys, Lys-Arg, Arg-Arg or Lys-Lys.

2. The method of claim 1, wherein the disease or disorder is obesity or type II diabetes.

3. The method of claim 1, wherein the amount of the peptide is in the range of from about 10 μg/kg body weight to about 5 mg/kg body weight.

4. The method of claim 1, wherein the pharmaceutical composition further comprises another appetite-suppressing or satiety-inducing agent.

5. The method of claim 4, wherein the other appetite-suppressing or satiety-inducing agent is glucagon-like peptide-1.

6. The method of claim 1, wherein $X^1$ is $NH_2$.

7. The method of claim 1, wherein $X^2$ is Ala.

8. The method of claim 1, wherein $X^3$ is Ile.

9. The method of claim 1, wherein $X^4$ is Asn.

10. The method of claim 1, wherein $X^5$ is Ala.

11. The method of claim 1, wherein $X^6$ is Arg.

12. The method of claim 1, wherein $X^7$ is Ile.

13. The method of claim 1, wherein $X^8$ is Gln.

14. The method of claim 1, wherein $X^9$ is OH.

15. The method of claim 1, wherein the peptide has an amino acid sequence of

HADGSFSDEMNTILDNLAARDFINWLIQ TKITD (SEQ ID NO:5).

16. The method of claim 1, wherein the peptide has an amino acid sequence of

HADGSFSDEMNTILDNLATRDFINWLIQ TKITD (SEQ ID NO:6).

17. The method of claim 1, wherein the peptide has an amino acid sequence of

HADGSFSDEMNTVLDNLATRDFINWLLH TKITD (SEQ ID NO:7).

* * * * *

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 35 amino acids
      (B) TYPE: amino acid
      (C) STRANDEDNESS: single
      (D) TOPOLOGY: linear    (ii) MOLECULE TYPE: None    (xi) SEQUENCE DESCRIPTION: SEQ ID NO:1:

Xaa His Xaa Asp Gly Ser Phe Ser Asp Glu Met Asn Thr Xaa Leu Asp
 1             5                  10              15

Xaa Leu Ala Xaa Xaa Asp Phe Ile Asn Trp Leu Xaa Xaa Thr Lys Ile
           20                25              30

Thr Asp Xaa
       35

(2) INFORMATION FOR SEQ ID NO:2:

(i) SEQUENCE CHARACTERISTICS:
             (A) LENGTH: 15 amino acids
             (B) TYPE: amino acid
             (C) STRANDEDNESS: single
             (D) TOPOLOGY: linear (ii) MOLECULE TYPE: None (xi) SEQUENCE DESCRIPTION: SEQ ID NO:2:

Asp Phe Pro Glu Glu Val Ala Ile Val Glu Glu Leu Gly Arg Arg
1               5                  10                  15

(2) INFORMATION FOR SEQ ID NO:3:

(i) SEQUENCE CHARACTERISTICS:
             (A) LENGTH: 15 amino acids
             (B) TYPE: amino acid
             (C) STRANDEDNESS: single
             (D) TOPOLOGY: linear (ii) MOLECULE TYPE: None (xi) SEQUENCE DESCRIPTION: SEQ ID NO:3:

Asp Phe Pro Glu Glu Val Thr Ile Val Glu Glu Leu Gly Arg Arg
1               5                  10                  15

(2) INFORMATION FOR SEQ ID NO:4:

(i) SEQUENCE CHARACTERISTICS:
             (A) LENGTH: 15 amino acids
             (B) TYPE: amino acid
             (C) STRANDEDNESS: single
             (D) TOPOLOGY: linear (ii) MOLECULE TYPE: None (xi) SEQUENCE DESCRIPTION: SEQ ID NO:4:

Asp Phe Pro Glu Glu Val Asn Ile Val Glu Glu Leu Arg Arg Arg
1               5                  10                  15

(2) INFORMATION FOR SEQ ID NO:5:

(i) SEQUENCE CHARACTERISTICS:
             (A) LENGTH: 33 amino acids
             (B) TYPE: amino acid
             (C) STRANDEDNESS: single
             (D) TOPOLOGY: linear (ii) MOLECULE TYPE: None (xi) SEQUENCE DESCRIPTION: SEQ ID NO:5:

His Ala Asp Gly Ser Phe Ser Asp Glu Met Asn Thr Ile Leu Asp Asn
1               5                  10                  15

Leu Ala Ala Arg Asp Phe Ile Asn Trp Leu Ile Gln Thr Lys Ile Thr
                20                  25                  30

Asp (2) INFORMATION FOR SEQ ID NO:6:

(i) SEQUENCE CHARACTERISTICS:
             (A) LENGTH: 33 amino acids
             (B) TYPE: amino acid
             (C) STRANDEDNESS: single
             (D) TOPOLOGY: linear (ii) MOLECULE TYPE: None (xi) SEQUENCE DESCRIPTION: SEQ ID NO:6:

His Ala Asp Gly Ser Phe Ser Asp Glu Met Asn Thr Ile Leu Asp Asn

```
             1               5              10              15

Leu Ala Thr Arg Asp Phe Ile Asn Trp Leu Ile Gln Thr Lys Ile Thr
                     20              25              30

Asp (2) INFORMATION FOR SEQ ID NO:7:

(i) SEQUENCE CHARACTERISTICS:
         (A) LENGTH: 33 amino acids
         (B) TYPE: amino acid
         (C) STRANDEDNESS: single
         (D) TOPOLOGY: linear (ii) MOLECULE TYPE: None (xi) SEQUENCE DESCRIPTION: SEQ ID NO:7:

His Ala Asp Gly Ser Phe Ser Asp Glu Met Asn Thr Val Leu Asp Asn
 1               5              10              15

Leu Ala Thr Arg Asp Phe Ile Asn Trp Leu Leu His Thr Lys Ile Thr
                     20              25              30

Asp (2) INFORMATION FOR SEQ ID NO:8:

(i) SEQUENCE CHARACTERISTICS:
         (A) LENGTH: 48 amino acids
         (B) TYPE: amino acid
         (C) STRANDEDNESS: single
         (D) TOPOLOGY: linear (ii) MOLECULE TYPE: None (xi) SEQUENCE DESCRIPTION: SEQ ID NO:8:

Asp Phe Pro Glu Glu Val Ala Ile Ala Glu Glu Leu Gly Arg Arg His
 1               5              10              15

Ala Asp Gly Ser Phe Ser Asp Glu Met Asn Thr Ile Leu Asp Asn Leu
                     20              25              30

Ala Thr Arg Asp Phe Ile Asn Trp Leu Ile Gln Thr Lys Ile Thr Asp
             35              40              45

(2) INFORMATION FOR SEQ ID NO:9:

(i) SEQUENCE CHARACTERISTICS:
         (A) LENGTH: 36 amino acids
         (B) TYPE: amino acid
         (C) STRANDEDNESS: single
         (D) TOPOLOGY: linear (ii) MOLECULE TYPE: None (xi) SEQUENCE DESCRIPTION: SEQ ID NO:9:

His Asp Glu Phe Glu Arg His Ala Glu Gly Thr Phe Thr Ser Asp Val
 1               5              10              15

Ser Ser Tyr Leu Glu Gly Gln Ala Ala Lys Glu Phe Ile Ala Trp Leu
                     20              25              30

Val Lys Gly Arg
             35
```